United States Patent
Polak et al.

(10) Patent No.: US 10,306,376 B2
(45) Date of Patent: *May 28, 2019

(54) BINAURAL COCHLEAR IMPLANT PROCESSING

(71) Applicant: MED-EL Elektromedizinische Geraete GmbH, Innsbruck (AT)

(72) Inventors: Marek Polak, Innsbruck (AT); Abdulrahman Abdullah Hagr, Riyadh (SA)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,021

(22) Filed: Jul. 5, 2018

(65) Prior Publication Data

US 2018/0317023 A1 Nov. 1, 2018

Related U.S. Application Data

(63) Continuation of application No. 15/005,046, filed on Jan. 25, 2016, now Pat. No. 10,038,959, which is a (Continued)

(51) Int. Cl.
*H04R 25/00* (2006.01)
*A61N 1/36* (2006.01)

(52) U.S. Cl.
CPC ....... *H04R 25/407* (2013.01); *A61N 1/36036* (2017.08); *H04R 25/505* (2013.01); (Continued)

(58) Field of Classification Search
CPC .... H04R 25/40; H04R 25/405; H04R 25/407; H04R 25/50; H04R 25/502; H04R 25/505; (Continued)

(56) References Cited

U.S. PATENT DOCUMENTS 10,038,959 B2 * 7/2018 Polak ............... H04R 25/407
2002/0037087 A1 3/2002 Allegro et al.
(Continued)

FOREIGN PATENT DOCUMENTS

WO WO 2013/101088 A1 7/2013

OTHER PUBLICATIONS

International Searching Authority, Authorized Officer Blaine R. Copenheaver, International Search Report and Written Opinion, PCT/US2014/047118, dated Nov. 28, 2014, 13 pages.
European Patent Office, Extended European Search Report, Application No. 14830201.1, dated Feb. 17, 2017, 8 pages.

*Primary Examiner* — Joshua Kaufman
(74) *Attorney, Agent, or Firm* — Sunstein Kann Murphy & Timbers LLP

(57) ABSTRACT

A sound processing arrangement is described for a patient with a bilateral cochlear implant system having implanted electrode arrays in each ear. There is a left-side sensing microphone and a right-side sensing microphone, each configured for sensing the sound environment surrounding the patient and generating corresponding microphone signals. A sound object identification module is configured for analyzing the microphone signals to identify one or more sound objects within the sound environment. A sound object selection module is configured for processing the microphone signals to generate a sound object signal for each of the one or more sound objects. A stimulation side selector module is configured for selecting on which side or sides of the bilateral cochlear implant arrangement to process each sound object signal. One or more sound processors processes the sound object signals to generate stimulation signals to the implanted electrode arrays on the selected side or sides.

15 Claims, 4 Drawing Sheets

Related U.S. Application Data continuation-in-part of application No. PCT/US2014/047118, filed on Jul. 18, 2014.

(60) Provisional application No. 61/857,756, filed on Jul. 24, 2013.

(52) U.S. Cl.
CPC ......... *H04R 25/552* (2013.01); *H04R 25/606* (2013.01); *H04R 2225/43* (2013.01); *H04R 2225/67* (2013.01); *H04R 2430/20* (2013.01)

(58) Field of Classification Search
CPC .............. H04R 25/552; H04R 2225/41; H04R 2225/43; H04R 2430/03; H04R 2430/20; A61N 1/36032
See application file for complete search history.

(56) References Cited

U.S. PATENT DOCUMENTS

| | | |
|---|---|---|
| 2003/0171786 A1 | 9/2003 | Blamey et al. |
| 2004/0172101 A1 | 9/2004 | Van Hoesel |
| 2009/0097681 A1 | 4/2009 | Puria et al. |
| 2009/0304187 A1 | 12/2009 | Dittberner |
| 2010/0067707 A1 | 3/2010 | Schwerdtner |
| 2010/0135500 A1 | 6/2010 | Derleth et al. |
| 2010/0246872 A1 | 9/2010 | Ochoco et al. |
| 2010/0310084 A1 | 12/2010 | Hersbach |
| 2010/0312308 A1 | 12/2010 | Busby |
| 2011/0125218 A1* | 5/2011 | Busby ................ A61N 1/36032 607/57 |
| 2011/0238176 A1 | 9/2011 | Bradley et al. |
| 2012/0128164 A1 | 5/2012 | Blamey |
| 2014/0330344 A1 | 11/2014 | Mishra et al. |

* cited by examiner

BINAURAL COCHLEAR IMPLANT PROCESSING

This application is a continuation of U.S. patent application Ser. No. 15/005,046, filed Jan. 25, 2016, which in turn is a continuation-in-part of Patent Cooperation Treaty Application PCT/US2014/047118, filed Jul. 18, 2014, which in turn claims priority from U.S. Provisional Patent Application 61/857,756, filed Jul. 24, 2014, each of which are incorporated herein by reference in their entireties.

FIELD OF THE INVENTION

The present invention relates to audio signal processing in cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant processor 108. Besides receiving the processed audio information, the implant processor 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

It once was commonly the case that cochlear implant systems were unilateral systems with only one ear being implanted with an electrode array that delivers electrical stimulation signals to the implanted ear. More commonly today, cochlear implant systems often are bilateral with both ears receiving implanted electrode arrays that deliver stimulation signals to the implanted ears.

The human auditory processing system segregates specific sound objects from complex auditory scenes using several binaural cues such as interaural time and level differences (ITD/ILD) and monaural cues such as harmonicity or common onset. This process is known as auditory scene analysis (ASA) as described more fully in A. S. Bregman *Auditory Scene Analysis: The Perceptual Organization of Sound*, MIT Press, Cambridge, Mass. (1990), incorporated herein by reference. Hearing impaired patients have difficulties successfully performing such an auditory scene analysis even with a hearing prosthesis such as a cochlear implant. Because of such problems, cochlear implant users often struggle to listen to a single individual sound source within a mixture of multiple sound sources as in a noisy sound environment. In the case of understanding speech, this translates into reduced speech intelligibility. In the case of music, musical perception is degraded due to the inability to successfully isolate and follow individual instruments.

U.S. Patent Publication 20100135500 describes a binaural hearing system with microphones on either side of the patient's head based on comparing the relative signal-to-noise ratios from each microphone. But there is no suggestion as to analysis and processing of sound objects in the surrounding sound environment.

WO 2013/101088 by Mishra stated that in prior art systems the sensed ipsilateral and contralateral signals were "compared as a whole and select one of them for presentation to the patient based on the comparison." Mishra proposed to compare the ipsilateral and contralateral signals on a channel-by-channel comparison, selectively amplifying the corresponding ipsilateral and contralateral signals (FIGS. 4 and 6) and then finally mixing the modified channel signals which was forwarded to the implanted cochlear implant. This approach does not consider components of an audio signal which may be correspond to the same sound object, e.g. the fundamental and first and/or second harmonic may be treated in different ways (different gains) and thus the sound object may be distorted.

SUMMARY OF THE INVENTION

Embodiments of the present invention are directed to a sound processing arrangement for a patient with a bilateral cochlear implant system having implanted electrode arrays in each ear. There is a left-side sensing microphone and a right-side sensing microphone, each configured for sensing the sound environment surrounding the patient and generating corresponding microphone signal outputs. A sound object identification module is configured for analyzing the microphone signals to identify one or more sound objects within the sound environment. A sound object selection module is configured for processing the microphone signals to generate a sound object signal for each of the one or more sound objects. A stimulation side selector module is configured for selecting on which side or sides of the bilateral cochlear implant arrangement to process each sound object signal. One or more sound processors processes the sound object signals to generate stimulation signals to the implanted electrode arrays on the selected side or sides.

In a specific embodiment, the one or more sound processors may process the sound object signals based on adjusting a phase component and/or an amplitude component of each sound object signal. The stimulation side selector module may be configured for using sound object time and/or amplitude difference components in the microphone signals to select on which side or sides of the bilateral cochlear implant arrangement to process each sound object signal. The sensing microphones may be located next to the ear on each side of the patient's head, or in the ear canal on each side of the patient's head.

DETAILED DESCRIPTION OF SPECIFIC EMBODIMENTS

Embodiments of the present invention are directed to sound processing arrangements and methods for a listener with a cochlear implant system that performs real time identification, selection and processing of sound objects in the surrounding sound environment. Examples of such sound objects include voices of individuals, musical instruments, and more generally, any noise generating objects such as cars, etc. Sound objects comprise several (or all) characteristic frequency features of a specific sound source such as the fundamental frequency and higher harmonics, or a specific frequency characteristic. In general, sound object are sets of complex sounds coming from a single exact position at a certain time and having specific frequency characteristics. The inventive approach identifies sound objects in both left-side and right-side microphone signals, and thereby does not treat the entire signals as a whole, but rather the individual sound objects themselves are treated as a whole, and entire sound objects are mixed. This produces binaural sound processing in unilateral and bilateral cochlear implant systems with more accurate timing and level information for the sound objects, thereby providing improved localization and better hearing of sound events.

Figure 1:
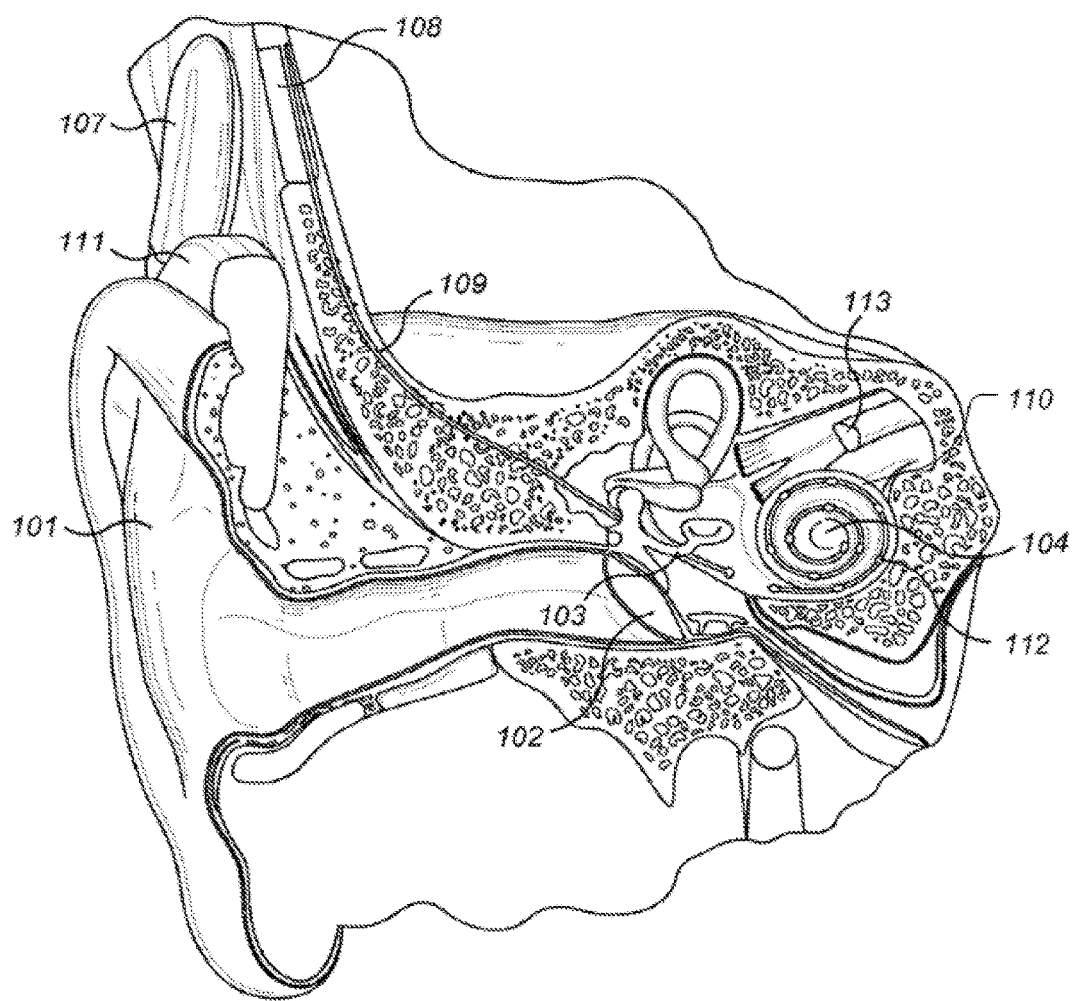
FIG. 1 shows elements of a human ear and cochlear implant system.
Figure 2:
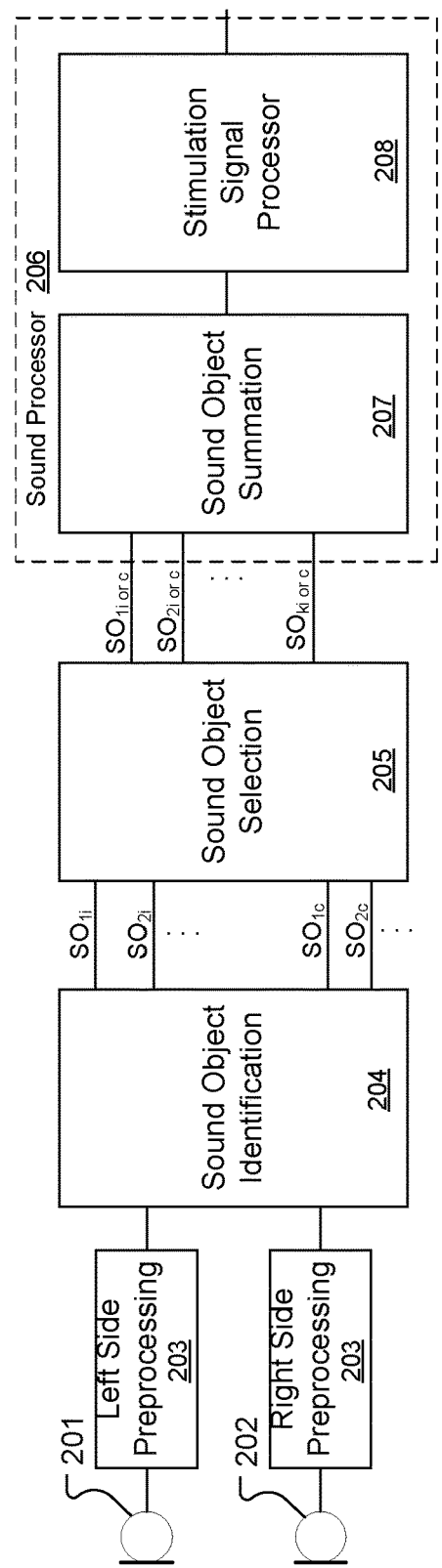
FIG. 2 shows various functional blocks in a sound processing arrangement for a unilateral cochlear implant system according to one embodiment of the present invention.

FIG. 2 shows functional blocks in an embodiment for a unilateral cochlear implant system where a left-side microphone 201 and a right-side microphone 202, are each configured for sensing the sound environment surrounding the patient and generating corresponding microphone signals. The left-side and right-side microphones 201 and 202 may be located next to the ear or in the ear canal on each side of the patient's head. Typically, each microphone signal may be initially processed by one or more preprocessor modules 203 to initially analyze and adjust the microphone signals.

A sound object identification module 204 is configured for analyzing the microphone signals in real time together with an analysis of the acoustic properties of the sound environment to identify the individual sound objects (SO) that are present within the sound environment. For each $k^{th}$ identified sound object, the sound object identification module 204 calculates two sound object subsets, $SO_{ki}$ and $SO_{kc}$.

A sound object selection module 205 is configured for processing the microphone signals to generate a sound object signal for each of the one or more sound objects. For example, the sound object selection module 205 may use sound object time difference components (i.e., phase difference) and/or sound object amplitude components in the microphone signals to select the sensing microphone closer to a given sound object to enhance its microphone signal to produce the corresponding sound object signal. If both microphone signals are substantially identical, the microphone closer to a sound object will provide a stronger signal and that signal will arrive earlier, and in this way, the sound object selection module 205 can select the stronger and earlier microphone signal for each sound object for processing to generate the corresponding sound object signal. For each sound object, the sound object selection module 205 outputs only the selected sound object signal. If the sound object selection module 205 does not identify any sound objects as present, then the sound may be processed from one microphone only, preferably from the left-side (ipsilateral) sensing microphone 201.

Figure 3:
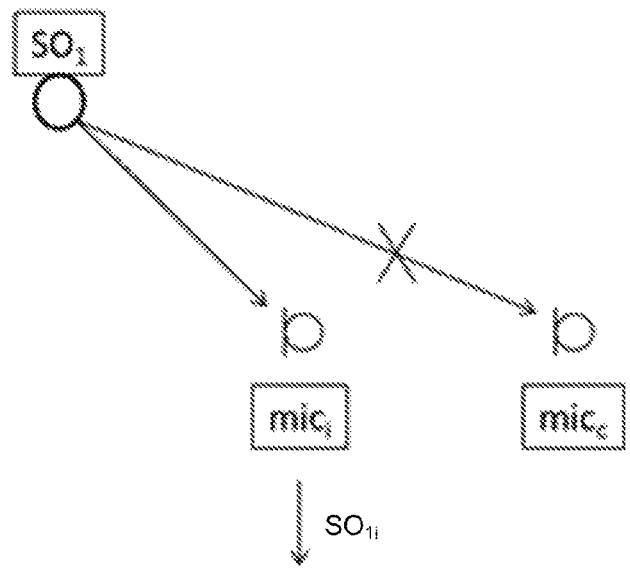
FIG. 3 shows an example situation for a single sound object which is closer to the ipsilateral microphone.
Figure 4:
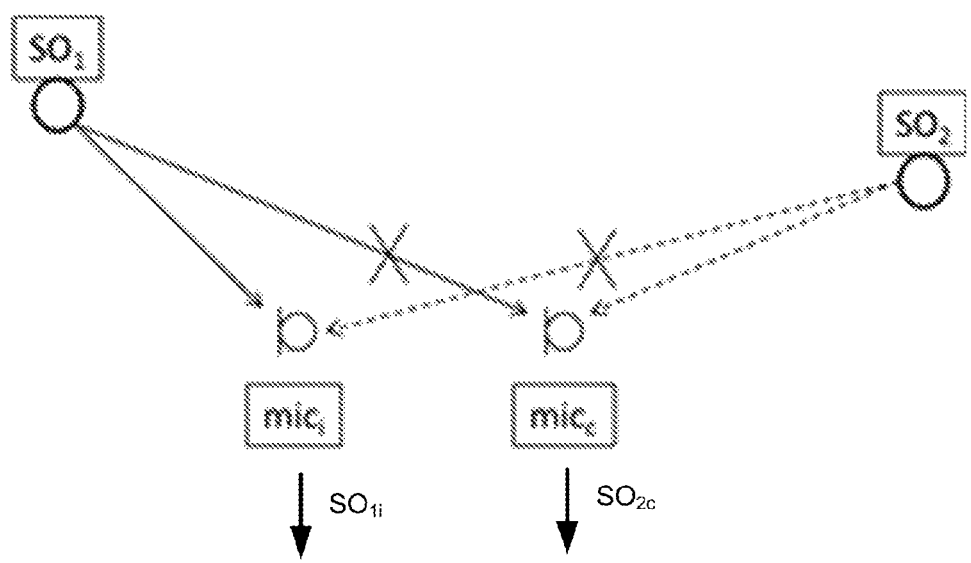
FIG. 4 shows an example situation for two sound objects.

FIG. 3 shows an example situation where a given sound object ($SO_1$) is identified to be closer to the ipsilateral left-side sensing microphone. The sound object selection module 205 in FIG. 2 will select only the left-side microphone signal for use as the sound object signal. FIG. 4 shows another situation with two different sound objects, one of which ($SO_1$) is closer to the left-side side and the other of which ($SO_2$) is closer to the right-side side. The sound object selection module 205 selects only $SO_{1i}$ and $SO_{2c}$ as sound object signals for output.

A sound processor 206 includes a sound object summation module 207 that combines the sound object signals from the sound object selection module 205 and a stimulation signal processor 208 that generates one or more stimulation signals to the cochlear implant based on user-specific fitting characteristics. The sound processor 206 may combine the sound object signals based on adjusting a phase component and/or an amplitude component of each sound object signal.

The entire system operates in real time so as to correctly track moving sound objects. If the $SO_1$ in FIG. 3 were to be moving from left to right, the $SO_{1c}$ microphone signal will be selected as the $SO_1$ sound object signal as soon as $SO_1$ is identified to be closer to the right-side microphone 202. The system components may be encased in a processor housing that may be worn either on the body (e.g., behind the ear) or that may be fully implantable.

The foregoing discussion relates to a unilateral cochlear implant system where the recipient patient has just one implanted ear. Similar approaches can also be applied in bilateral systems where both ears are implanted. Basically, as in a unilateral system, the sound objects in a bilateral system are analyzed in real time (in one or more signal processor), but the selected individual sound objects are only presented to the ear which is closer to the sound object.

Figure 5:
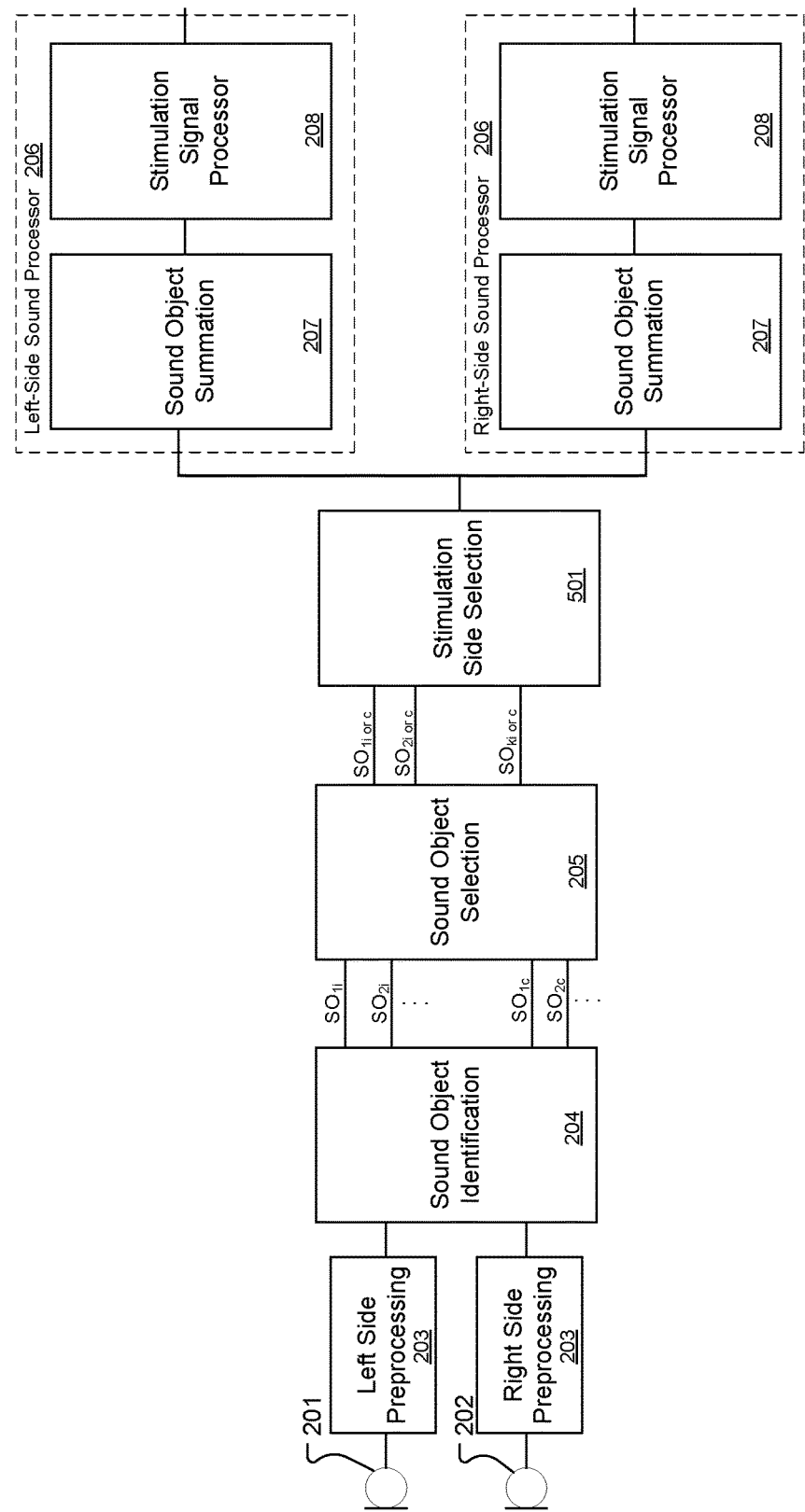
FIG. 5 shows various functional blocks in a sound processing arrangement for a bilateral cochlear implant system according to one embodiment of the present invention.

FIG. 5 shows various functional blocks in a sound processing arrangement for a bilateral cochlear implant system according to one embodiment of the present invention, where blocks 201-205 are as in the unilateral embodiment in FIG. 2. And the sound object processing blocks 206/208 are each implanted for each ear, but otherwise are the same as in FIG. 2. The two cochlear implants and their respective processing blocks are communicatively connected (wired or wireless) to exchange information as described below. In addition to the blocks shown and described with respect to FIG. 2, the system in FIG. 5 also includes a stimulation side selection module 501 that receives the sound object signals from the sound object selection module 205 and selects which side or sides to use for stimulation. Of course, modules 204, 205 and 501 can also be combined into a single physical module. If the selected subset with the stronger and earlier phase is obtained from the left-side sensing microphone 201, then only the left-side cochlear implant is selected for stimulation, and that sound object information is not provided to the cochlear implant on the right-side side, and vice versa. So in FIG. 4, sound object signal $SO_{1i}$ would only be presented to one of the cochlear implants, and sound object signal $SO_{2c}$ only to the other one.

In a specific implementation for bilateral cochlear implant, the maximum interaural time difference phase (or time) delay (ITD) between the two ears should be taken into account. This ITD typically may be approximately 0.66 ms (considering the speed of the sound at sea level). Thus the length of the time window used for comparison of the left- and right-side sampled signal should be larger than 0.66 ms. The sampled amplitudes from both time windows of the sensing microphones can be compared. Then in order to select corresponding time windows of both sides which have a sufficiently large overlap in time such that they contain audio information of the same audio events, appropriate information/commands need to be exchanged between the processors before starting the comparison. Each sample or combination of samples within the time window may need to be compared with samples or combination of samples within the time window from the sensing microphone on the other side. This comparison may be performed systematically or according to predefined heuristics. So far, this may be the same implementation as in the situation described above in connection with a single cochlear implant and a contralateral side sensing microphone only. In any case, this comparison can create a high workload for the processors, and so a work load sharing distribution between both processors may be a useful solution. But if the available communication rate between the processors is relatively low, it may be better to perform the comparison in just one of the two processors. After completion of this comparison, this process results in a determination of which side or sides is preferred for further processing for the identified sound objects. The selected time windows may be chosen continuously (i.e. a window is defined after each new sample), or selected after a certain period of time (i.e at an integer number of samples after that sample from which the previous windows has started). This time selection may be predefined or may depend on the previously evaluated time window samples.

Looking again at the scenario in FIG. 3 and keeping in mind that there are communicatively coupled cochlear implants on both sides, besides determining the preferred sensing microphone to use, the preferable stimulation side (left- or right-side implant) is also established. This may lead to a significantly improved sound localization ability of the patient.

After the sound objects are distinguished, the processed amplitude for the dominant implant may be further adjusted. Such amplitude adjustment may be performed after the processing signal is split into frequency bands as known from state-of-the-art cochlear implant systems (part of the stimulation signal processor 208 in FIG. 5). The amplitude adjustment may be dependent from the frequency and the sound object position in order to account for effects such as head shadow and/or squelch. Such amplitude adjustment may also be favorable in the case of a unilateral implant with a contralateral microphone as described above.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A sound processing arrangement for a patient with a bilateral cochlear implant system having implanted electrode arrays in each ear, the system comprising:
  an ipsilateral left-side sensing microphone and a contralateral right-side sensing microphone, each configured for sensing the sound environment surrounding the patient and generating corresponding microphone signals;
  a sound object identification module configured for analyzing the microphone signals to identify a plurality of sound objects $SO_k$ within the sound environment, the sound object identification module providing for each $k^{th}$ identified sound object $SO_k$, two sound object subsets, $SO_{kI}$ received from the ipsilateral left-side sensing microphone and $SO_{kC}$ received from the contralateral right-side sensing microphone;
  a sound object selection module configured to select, for each $k^{th}$ identified sound object, either $SO_{kI}$ or $SO_{kC}$ for use as a sound object signal for each of the plurality of sound objects;

a stimulation side selector module configured for selecting, for each sound object signal, which side or sides of the bilateral cochlear implant arrangement to use for stimulation; and one or more sound processors for processing each sound object signal so as to generate a stimulation signal to the implanted electrode arrays on the side or sides selected for the sound signal object.

2. An arrangement according to claim 1, wherein the one or more sound processors process the sound object signals based on adjusting a phase component of each sound object signal.

3. An arrangement according to claim 1, wherein the one or more sound processors process the sound object signals based on adjusting an amplitude component of each sound object signal.

4. An arrangement according to claim 1, wherein the stimulation side selector module is configured for using sound object time difference components in the microphone signals to select, for each sound object, which side or sides of the bilateral cochlear implant arrangement to use for stimulation.

5. An arrangement according to claim 1, wherein the stimulation side selector module is configured for using sound object amplitude difference components in the microphone signals to select, for each sound object, which side or sides of the bilateral cochlear implant arrangement to use for stimulation.

6. An arrangement according to claim 1, wherein the sensing microphones are located next to the ear on each side of the patient's head.

7. An arrangement according to claim 1, wherein the sensing microphones are located in the ear canal on each side of the patient's head.

8. A method of processing sound signals for a patient with a bilateral cochlear implant system having implanted electrode arrays in each ear, the method comprising:

sensing the sound environment surrounding the patient with an ipsilateral left-side sensing microphone and a contralateral right-side sensing microphone and generating corresponding microphone signals;

analyzing the microphone signals to identify a plurality of sound objects $SO_k$ within the sound environment, and providing for each $k^{th}$ identified sound object $SO_k$, two sound object subsets, $SO_{kI}$ received from the ipsilateral left-side sensing microphone and $SO_{kC}$ received from the contralateral right-side sensing microphone;

selecting for each $k^{th}$ identified sound object, either $SO_{kI}$ or $SO_{kC}$ for use as a sound object signal for each of the plurality of sound objects $SO_k$;

selecting, for each sound object signal, which side or sides of the bilateral cochlear implant arrangement to use for stimulation; and processing each sound object signal so as to generate a stimulation signal to the implanted electrode array on the side or sides selected for the sound signal object.

9. A method according to claim 8, wherein processing the sound object signals includes adjusting a phase component of each sound object signal.

10. A method according to claim 8, wherein processing the sound object signals includes adjusting an amplitude component of each sound object signal.

11. A method according to claim 8, wherein sound object time difference components in the microphone signals are used for selecting, for each sound object, which side or sides of the bilateral cochlear implant arrangement to use for stimulation.

12. A method according to claim 8, wherein sound object amplitude difference components in the microphone signals are used for selecting for each sound object, which side or sides of the bilateral cochlear implant arrangement to use for stimulation.

13. A method according to claim 8, wherein the sensing microphones are located next to the ear on each side of the patient's head.

14. A method according to claim 8, wherein the sensing microphones are located in the ear canal on each side of the patient's head.

15. A sound processing arrangement for a patient with a unilateral cochlear implant system having an implanted electrode array in one ear, the system comprising:

an ipsilateral left-side sensing microphone and a contralateral right-side sensing microphone, each configured for sensing the sound environment surrounding the patient and generating corresponding microphone signals;

a sound object identification module configured for analyzing the microphone signals to identify a plurality of sound objects $SO_k$ within the sound environment, and providing for each $k^{th}$ identified sound object $SO_k$, two sound object subsets, $SO_{kI}$ received from the ipsilateral left-side sensing microphone and $SO_{kC}$ received from the contralateral right-side sensing microphone;

a sound object selection module configured to select, for each $k^{th}$ identified sound object, either $SO_{kI}$ or $SO_{kC}$ for use as a sound object signal for each of the plurality of sound objects $SO_k$, wherein $SO_{kI}$ is selected if the ipsilateral left-side sensing microphone is closer to the sound object $SO_k$, and wherein $SO_{kC}$ is selected if the contralateral right-side sensing microphone is closer to the sound object $SO_k$; and a sound processor configured for processing the sound object signals to generate stimulation signals to the implanted electrode array.

* * * * *